United States Patent [19]
Guldner et al.

[11] Patent Number: 5,814,102
[45] Date of Patent: Sep. 29, 1998

[54] PROCESS FOR TRAINING A SKELETAL MUSCLE FOR A BIOMECHANICAL HEART AND BIOMECHANICAL HEART USING SUCH A MUSCLE

[76] Inventors: Norbert Guldner, Stettinerstrasse 12h, 23617-Stockeldorf, Germany; Sylvain Thuaudet, Rue du Vieux Lavoir Cainet, 14480-le Fresne Camilly, France

[21] Appl. No.: 549,721
[22] PCT Filed: May 13, 1994
[86] PCT No.: PCT/FR94/00571
§ 371 Date: Dec. 14, 1995
§ 102(e) Date: Dec. 14, 1995
[87] PCT Pub. No.: WO94/26326
PCT Pub. Date: Nov. 24, 1994

[30] Foreign Application Priority Data

| May 14, 1993 | [FR] | France | 93 05853 |
| Aug. 13, 1993 | [FR] | France | 93 09954 |
| Oct. 11, 1993 | [FR] | France | 93 12075 |

[51] Int. Cl.$^6$ .................................................. A61M 1/10
[52] U.S. Cl. .................................................. 623/3; 600/16
[58] Field of Search .................................. 623/3, 16–17; 600/16–18

[56] References Cited

U.S. PATENT DOCUMENTS

| 4,813,952 | 3/1989 | Khalafalla | 623/3 |
| 5,007,927 | 4/1991 | Badylak et al. | 623/3 |
| 5,098,442 | 3/1992 | Grandjean | 623/3 |

FOREIGN PATENT DOCUMENTS

| 92/05813 | 4/1992 | WIPO | 623/3 |

Primary Examiner—John G. Weiss
Assistant Examiner—Francis K. Cuddihy
Attorney, Agent, or Firm—Young & Thompson

[57] ABSTRACT

A method for dynamically training a skeletal muscle (1) to be used for a biomechanical heart involves wrapping the skeletal muscle (1) around a deformable training device (2) which can contract, resistance to contraction being provided, and recover its initial form. The skeletal muscle (1) is stimulated by periodic electrical impulses. In a first stage, the skeletal muscle (1) is stimulated by electrical impulses at a frequency increasing with time, and in a second stage the contraction resistance of the deformable training device (2) is increased progressively, the first and second stages possibly overlapping slightly. A biomechanical heart operated by a skeletal muscle (1) having undergone the dynamic training is also disclosed.

14 Claims, 3 Drawing Sheets

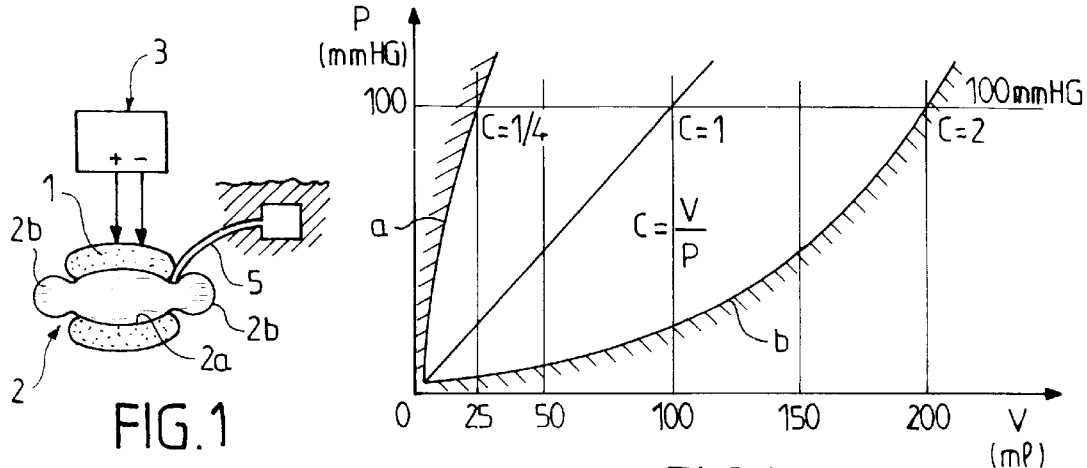
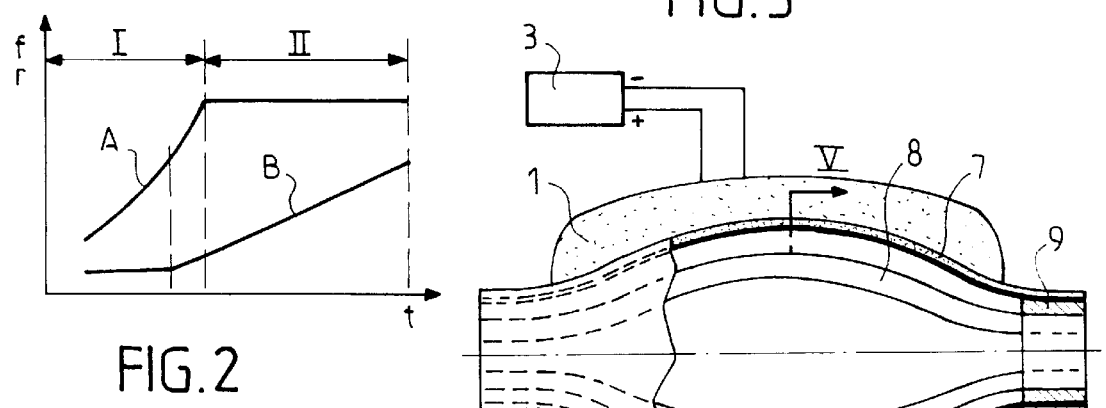
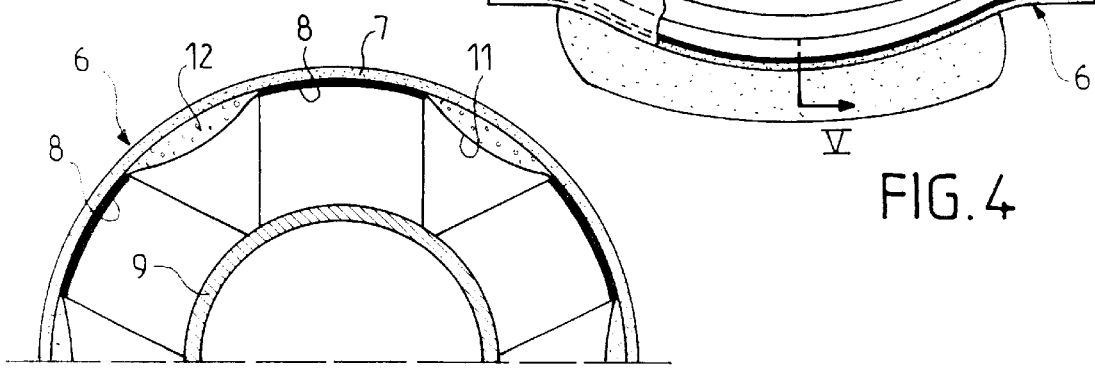
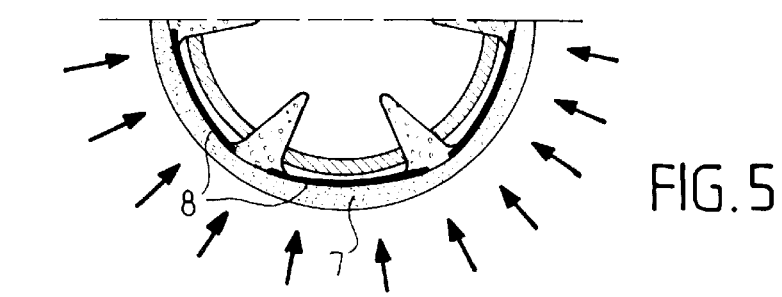

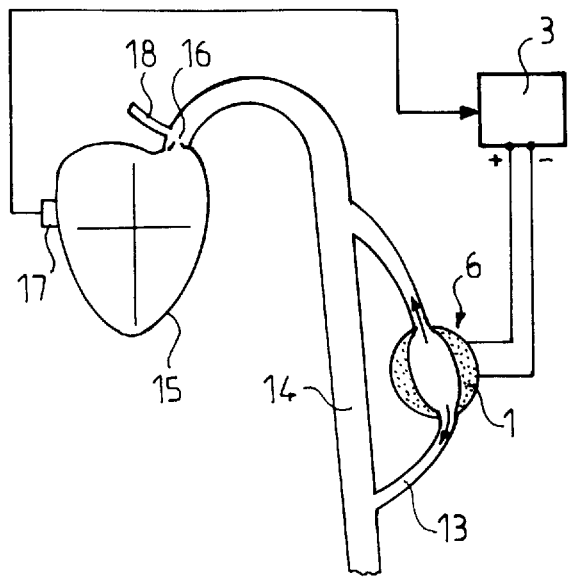
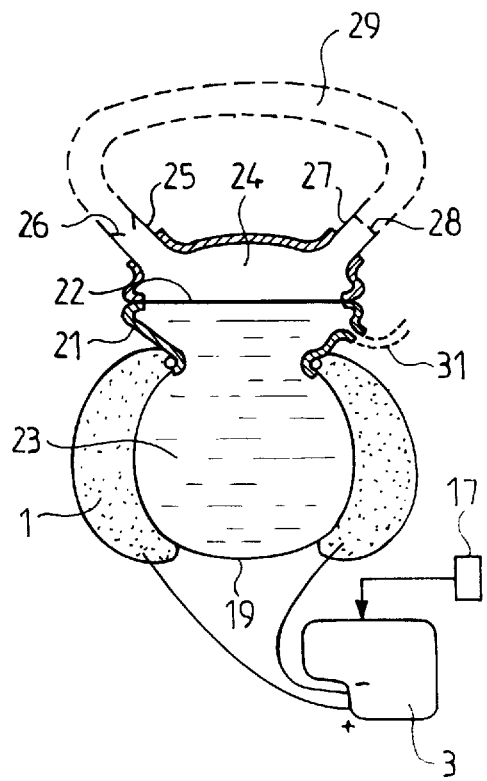
FIG. 6
FIG. 7
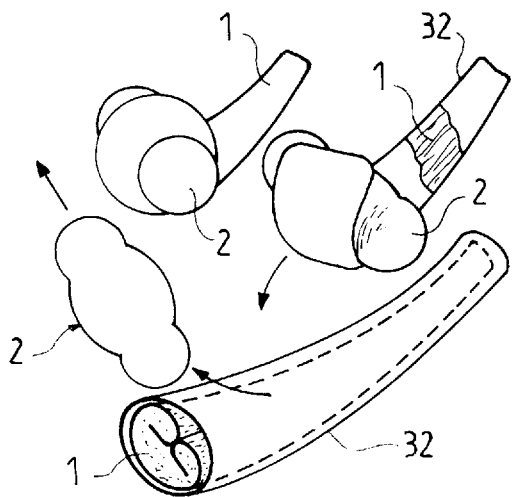
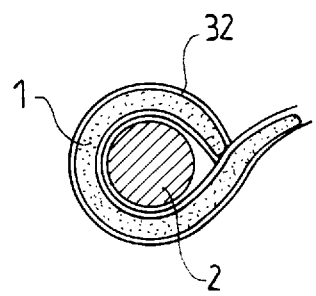
FIG. 8
FIG. 9

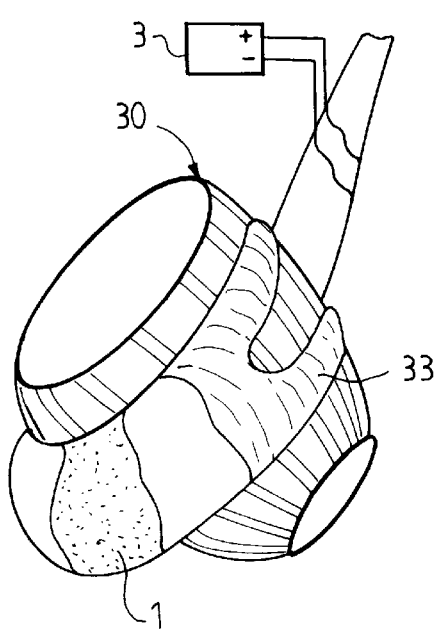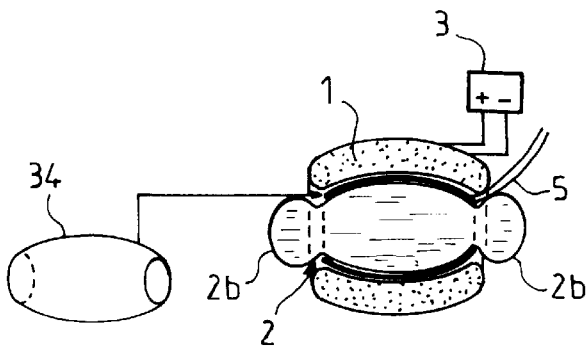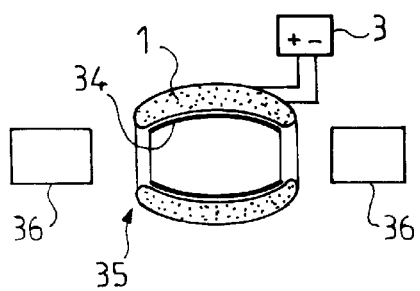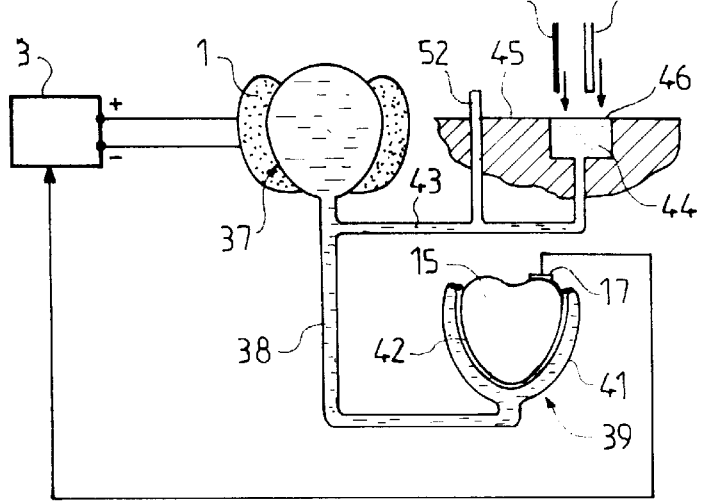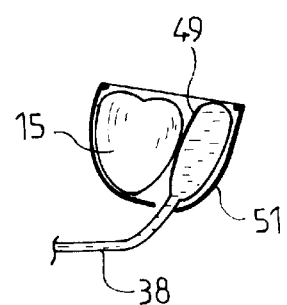
FIG.10
FIG.11
FIG.12
FIG.13
FIG.14

PROCESS FOR TRAINING A SKELETAL MUSCLE FOR A BIOMECHANICAL HEART AND BIOMECHANICAL HEART USING SUCH A MUSCLE

The present invention relates to a process for dynamically training a skeletal muscle for a biomechanical heart as well as a biomechanical heart using such a muscle.

It has already been proposed to provide a biomechanical heart in the form of a circulatory pump adapted to be completely implanted in the thoracic cage of a patient, particularly in the case of terminal cardiac insufficiency. This pump is actuated by a skeletal muscle, for example the large dorsal muscle, subjected to electrostimulation such that all the pulsing energy of the pump derives from the metabolism of the muscle which serves as a sort of motor. Such a biomechanical heart, using a skeletal muscle as motor, offers the advantage that it does not involve a rejection reaction of the mechanism because the muscle which is used belongs to the patient in whom the biomechanical heart is implanted.

So as to be able to use as a motor for such a biomechanical heart, a muscle which will not tire, with so-called type I fibers, it has already been proposed preliminarily to subject the muscle to dynamic training, as is described in these publications:

N. W. Guldner et al.; "Development and training of skeletal muscle ventricle with low preload"; J. Card. Surg., 1991; vol. 6, No 1.

N. W. Guldner et al.; "Dynamic training of skeletal muscle ventricles—a method to create high performance for muscle powered cardiac assist."; Fourth Vienna International Workshop on Functional Electrostimulation; Baden/Vienna, Sep. 24–27, 1992; ISBN 3-900928-08-9 1992.

This type of dynamic drive consists in wrapping the muscle about a drive device comprising an elastically deformable element with an internal chamber filled with liquid and terminating at its ends in inflatable bladders, such an apparatus being described in the document WO-A-9205813. To ensure drive of the muscle, it is connected to a myostimulator producing periodic electric stimulation pulses and when the muscle is thus excited by an electrical pulse, it contracts, which produces a contraction of the central chamber and an expulsion of the liquid toward the lateral bladders which inflate. When the muscle is no longer excited, between two successive electrical pulses and when it relaxes, the bladders deflate and the liquid returns to a central chamber which increases in volume, and the cycle can then be repeated.

The present invention relates to improvements in this process for training a muscle permitting obtaining a substantial increase of the muscular mass and its developed power.

To this end, the dynamic training process for a skeletal muscle adapted to be used in a biomechanical heart, in which the skeletal muscle is wrapped about a deformable drive apparatus adapted to contract, whilst opposing resistance to the contraction, and then to resume its initial shape and the skeletal muscle is stimulated, by means of periodic electrical pulses so as to produce its contraction and that of the deformable drive apparatus and their subsequent relaxation, is characterized in that during a first step the skeletal muscle is stimulated by means of electrical pulses having a frequency increasing as a function of time and in the course of a second step the resistance of the deformable drive apparatus to contraction is progressively increased, the first and second steps if desired somewhat overlapping.

There is also known from U.S. Pat. No. 5,007,927 a cardiac assistance device which is actuated by a skeletal muscle subjected to a stimulus supplied by a programmed pulse generator.

It is known that, in practice, such a device is only very little effective to the extent that the skeletal muscle used is incapable of supplying sufficient power for its actuation.

The present invention proposes to overcome this drawback by using as drive muscle a muscle trained according to the training process which is the object of the application, thus having been subjected to "mechanical" transformations conferring on it the necessary power for the proper actuation of the biomechanical heart.

The invention thus also has for its object a biomechanical heart using as a motor a skeletal muscle having been subjected to such dynamic training.

There will be described hereafter, by way of nonlimiting examples, various forms of embodiment of the present invention with reference to the accompanying drawings, in which:

FIG. 1 is a schematic view illustrating the process according to the invention for dynamically training a skeletal muscle adapted to be used in a biomechanical heart.

FIG. 2 is a diagram showing the variation as a function of time of the frequency of the electrical stimulation pulses and of the resistive mechanical load applied to the muscle during its training.

FIG. 3 is a diagram illustrating the range of variation of the pressure/volume characteristic for each of the inflatable bladders of the training apparatus.

FIG. 4 is an elevational view, in partial axial cross section, of a biomechanical ventricle according to the invention, with axial circulation of the blood flow.

FIG. 5 is a transverse cross sectional view, on a larger scale, taken on line V—V of FIG. 4, the upper portion of the figure representing the biomechanical ventricle in relaxed state whilst the lower half represents the ventricle in a contracted condition.

FIG. 6 is a schematic diagram of the use of a biomechanical ventricle according to the invention, with axial circulation, for cardiac assistance.

FIG. 7 is a schematic cross sectional view of a modified embodiment of a biomechanical ventricle with transverse circulation of the blood flow.

FIG. 8 is a schematic perspective view showing the different phases of training of a muscle disposed in a tubular envelope.

FIG. 9 is a transverse cross sectional view of the muscle and its envelope wrapped about the dynamic training apparatus.

FIG. 10 is a perspective view of a motor muscle of FIGS. 8 and 9 wrapped about a spring cage constituting a pericardiac device.

FIG. 11 is a schematic view showing a muscle wrapped about the dynamic training apparatus with the interposition of an intermediate envelope.

FIG. 12 is a schematic axial cross sectional view of the motor muscle and of its intermediate envelope obtained after the training period.

FIG. 13 is a schematic view of a modified embodiment of a pericardiac device comprising a hydraulic transmission system between the pump and the human heart.

FIG. 14 is a schematic cross sectional view of a modified embodiment of the receiver associated with the human heart.

In FIG. 1 is shown schematically the dynamic training process of a skeletal muscle 1, for example the large dorsal muscle, adapted to be used in a biomechanical heart according to the invention. This muscle 1 is wrapped about a dynamic training apparatus 2 and more particularly about a central chamber 2a filled with liquid and prolonged at its two ends by inflatable bladders 2b. The material constituting the central chamber 2a should not be elastic whilst the material forming the inflatable bladders 2b is. To train the muscle 1, first of all an electro-stimulation of this muscle is produced by connecting it to a myostimulator 3 which is thus a periodic electric pulse generator. When the muscle is excited by one of these pulses, it contracts, which gives rise to a reduction in volume of the central chamber 2a and an expulsion of the liquid from this chamber toward the elastic lateral bladders 2b which inflate, so that the training apparatus 2 opposes resistance to the contraction of the muscle 1. After the disappearance of the electrical excitation pulse, the muscle 1 relaxes and the resilient bladders 2b deflate ejecting the liquid which returns to the central chamber 2a. This central chamber 2a then inflates in turn, to resume at least its initial shape, whilst exerting a positive return force on the muscle 1, which force is directed externally and oriented in a reverse direction from that exerted by the muscle during its contraction. In the process according to the invention there is used on the one hand an incremental variation of the frequency of the electrical pulses of the generator 3 and, on the other hand, an incremental variation of the resistive mechanical load which opposes the contraction of the muscle 1. To this end, the internal volume of the training apparatus 2 is connected to a catheter 5 communicating with a chamber implantable under the skin and permitting progressively increasing the quantity of liquid in the central chamber 2a and in the inflatable bladders 2b. During a first stage of training the muscle 1, indicated by I in FIG. 2, there are applied to this muscle electrical stimulation pulses whose frequency f progressively increases with time. One begins for example with a slow pulse, of the order of one pulse per minute (corresponding to a frequency of about 0.017 Hz of the stimulator) and then this frequency is progressively increased, for a period of time of the order of 6 to 10 weeks, until the normal cardiac rhythm of the order of 60 to 80 pulses per minute (frequency of 1 to 1.33 Hz in the stimulator). This increase in frequency f as a function of time t is illustrated by the curve A in FIG. 2. Moreover, the first stage of electrical stimulation I is followed by a second stage II in the course of which the resistance r opposed by the training apparatus 2 to the muscular contraction, is progressively increased, as is shown by the curve B. This increase in resistive load is obtained by a progressive introduction of liquid into the apparatus 2, by means of the device 5.

The combination of the first stage of electrical stimulation with increasing frequency and the second stage of progressive increase of the resistance to muscular contraction permits obtaining a notable increase in the muscular mass and of the power of the muscle. Thus according to experiments carried out on the large dorsal muscle of young cattle, a power of 10 watts has been achieved, whilst in healthy humans at rest the maximum power of the left ventricle is about 3 watts.

It is known that in certain subjects, it is possible to render partially simultaneous the two stages I and II, which is to say that it is possible at least during a certain time of overlap of the two stages, to increase both and progressively the frequency of excitation of the stimulator and the quantity of liquid introduced into the training apparatus 2.

According to a complimentary characteristic of the invention, the material constituting the two inflatable bladders 2b is constituted by a silicone of the elastic type forming the wall of the bladders and by polymeric ribs embedded in this wall such that there is obtained, for each of the inflatable bladders 2b, a pressure/volume characteristic comprised within the range delimited between the two limit curves a and b in FIG. 3. In this figure, the elasticity C of the inflatable bladders is given by the ratio between the volume V and the pressure P of each bladder. Best results have been obtained with a value of elasticity C comprised between ¼ (curve a) and 2 (curve b). In a particularly advantageous embodiment, the wall of each bladder 2b is constituted by three layers, namely an internal layer and an external layer of material known as "Rehau SI 1511" and an intermediate layer of a material known by the name "Dow Corning Q3-8111" or "Dow Corning MDX4-4210".

FIGS. 4 and 5 show an embodiment of a biomechanical heart according to the invention constituting a "ventricle" with axial circulation of blood flow, using as the motor a skeletal muscle driven dynamically in the manner described above. This biomechanical ventricle comprises a muscle 1, first trained as previously indicated, which is connected to a myostimulator 3 and is wrapped about a deformable tubular pumping cage 6. This cage 6, flexible and elastic, has a central portion of large diameter prolonged by two opposite end portions of smaller diameter. The tubular pumping cage 6 comprises a flexible external envelope 7, for example of silicone, and within this envelope several layers of outwardly convex curved spring blades 8, extending along all the length of the envelope 7, from one end to the other of the cage 6, and spaced about the axis of this cage 6. The ends of these spring blades 8 are embedded in two transverse annular stretchers 9 disposed respectively in the two open ends of the tubular cage 6. An internal membrane 11, which is athrombogenic, for example of polyurethane, extends within the cage 6, covering the spring blades 8 to which it adheres so as to delimit, between the spring blades 8, individual sealed chambers filled with the fluid 12. When the muscle 1 is not excited, which is to say when it is relaxed, the tubular cage 6 has a large diameter and in this case the membrane 11 delimits relatively flat chambers, as is shown in the upper portion of FIG. 5. On the contrary, when the muscle 1 is excited, the tubular cage 6 is contracted, as is shown in the lower portion of FIG. 5, the spring blades 8 are flattened and approach each other and the membrane 11, then forms chambers which project inwardly, between the spring blades 8, substantially in radial directions. When the muscle relaxes, the spring blades 8 permit the distension, which is to say the return of the tubular pumping cage 6, to its initial large volume condition.

FIG. 6 shows the use of the tubular pumping cage 6 provided in the manner shown in FIGS. 4 and 5, to constitute an extra-aortic counter-pulse device. The tubular pumping cage 6 whose muscle 1 is electrically connected to the myostimulator 3, is branched off into a conduit 13 from the aorta 14 of a patient whose heart is represented at 15. When the aortic valve 16 is closed (diastole), the myostimulator 3 sends, in synchronism with the left ventricular diastole, an electric pulse to the muscle 1 to stimulate it. Synchronization is ensured by a detector 17 which hears the cardiac pulses in contact with the heart 15 and is connected to the myostimulator 3. Because of the excitation of the muscle 1, the tubular pumping cage 6 is compressed and the blood is directed upstream and downstream, as is indicated by the arrows. The direction of the blood upstream results in an increase of circulation in the coronaries 18. By contrast, when the aortic valve is open (systole) the muscle 1 is not electrically stimulated, it relaxes and the tubular cage 6 dilates creating an under pressure favoring blood circulation in the aorta. This biomechanical ventricle with axial circulation of the blood flow can also be used in other topographical configurations, such as between the left atrium and the aorta, between the left ventricle and the aorta, between the right atrium and the pulmonary artery. In this case, the biomechanical ventricles will be provided with two connections, namely an inlet connection provided with an inlet valve and an outlet connection provided with an outlet valve.

In the modified embodiment of a biomechanical "ventricle" shown in FIG. 7, which is provided for transverse circulation of the blood flow, the muscle 1 surrounds a flexible inexpansible pocket 19 extending outside a hollow body 21, through an opening in this latter. The body 21 is separated into two portions by a sealing membrane 22 (lower piston) delimiting on the one hand a pumping chamber 23 within the flexible pocket 19, containing a liquid such as a physiological serum, and, on the other hand, an expulsion chamber 24. The expulsion chamber 24 is provided with two connections, namely an inlet connection 25 provided with an inlet valve 26, and an outlet connection 27 provided with an outlet valve 28.

The biomechanical "ventricle" shown in FIG. 7 can be used for partial or total assistance, as well as for the left heart, between the left ventricle and the aortal artery, as well as for the right heart between the right atrium and the pulmonary artery. In this case the inlet connections 25 and outlet connections 27 are branched from the circulatory system. It can be used without inlet valves and outlet valves in an aorto-aortic configuration of extra-aortic counter pulses.

The apparatus shown in FIG. 7 can also be used to ensure the dynamic training of the muscle 1. In this case, the inlet connections 25 and outlet connections 27 are not branched from the circulatory system but are interconnected by a conduit 29 which is then cut to disable it during passage toward operation, so as to connect the connections 25 and 27 to the circulatory system.

In FIG. 7 is also shown a catheter 31 which causes the pumping chamber 23 to communicate with a filling device for this pumping chamber with a propulsive liquid, during the second stage of the dynamic training process, so as to permit increasing progressively the quantity of liquid in the pumping chamber 23, and so as to measure regularly the pressure of this liquid to follow the course of the muscular performance. The catheter 31 can if desired be omitted during the passage to normal operation but it can also be left in place to serve as a measure of the pressure of the propulsion liquid.

FIGS. 8 and 9 show a modified embodiment in which the muscle 1 is first disposed, before its dynamic training, in a tubular sleeve 32 constituted by a polymeric membrane which protects the muscle during the dynamic training process and ensures its nonadherence to the surrounding tissues. The sleeve 32 is of any natural, artificial or synthetic polymeric material but preferably it is constituted by a polymer substituted particularly with fluorine, such as polymers of the polytetrafluoroethylene type.

FIG. 10 shows a pericardiac device comprising the muscle 1, about a tubular cage 30 which is flexible and elastic, open at its two ends. One of the openings of the cage 30 has a sufficiently large diameter to permit the introduction of a human heart within the cage 30. The stimulation of the muscle 1 then effects the contraction of the cage 30 and that of the human heart disposed tightly within this cage. If the muscle is insufficiently long, there can be provided a prolongation at Y 33, made of a resistant polymer, for example of Dacron or of PTFE.

FIGS. 11 and 12 show a modified embodiment in which, during dynamic training of the muscle, there is interposed between the muscle 1 and the dynamic training apparatus 2 a membrane 34 wrapped about an axle, with a continuous surface, open at its two ends. This membrane 34 is made preferably of a material "colonizable" by the conjunctive tissue. After the training phase, the flexible tubular "cage" 35 thus obtained comprises, on its outside, the muscle 1, and, within the interior, the membrane 34 adhering to the muscle and colonized by the cells of the conjunctive tissue. The cage 35 can be used directly as a pumping chamber and it can be connected to artificial prostheses 36.

FIG. 13 shows an embodiment of the pericardiac device in which the muscle 1 is wrapped about a flexible elastic cage 37, forming a pumping chamber or an emitter of pressure pulses, whose internal volume communicates, through a conduit 38, with a pocket 39 in the form of a bolus in which is disposed a human heart 15. The pocket 39 which forms a receiver for the pressure pulses, has a hollow wall and it comprises an inexpansible external envelope 41 and an expansible internal envelope 42 in contact with the heart. The flexible elastic cage 37, with variable pumping volume, is thus connected by a hydraulic transmission device to the pocket 39. When the cage 37 contracts, under the action of the muscle 1 electrically stimulated, it pumps liquid, via a conduit 38, to the interior of the pocket 39, in other words it creates a pressure pulse transmitted to the pocket 39. As its external envelope 41 is not expansible, the excess liquid arriving in the pocket causes an expansion of the internal envelope 42 and thus a contraction of the human heart 15.

The conduit 38 is connected, via a derivation conduit 43, to a chamber 44 located beneath the skin 45 of a patient enclosed by a perforable membrane 46. Through this membrane can be introduced a needle 47 for the resupply of propulsive liquid. Moreover, a needle 48 for measuring the pressure can also be introduced through the membrane 46.

In the modified embodiment shown in FIG. 14, the conduit 38 of the hydraulic transmission device empties into a pressure pulse receiver comprising an expansible envelope 49 disposed within an external inexpansible pocket 51, in the interior of which pocket is also located the human heart 15. The expansible envelope 49 is in contact on the one hand with the external pocket 51 and on the other hand with the human heart 15 so that the pressure pulses in the conduit 38 give rise to an increase in the volume of the expansible envelope 49 and a contraction of the heart 15.

There can also be provided, as is shown in FIG. 13, a tube 52 connected to the hydraulic transmission circuit, for example to the conduit 43 or 38. This tube permits the transcutaneous connection to a suction (aspiration) system for a short period. This transcutaneous connection can be omitted after several days when the internal surface of the hydraulic pocket 39 (for example of silicone), adheres permanently to the epicardium.

We claim:

1. A process for dynamic training of a skeletal muscle (1) adapted to be used in a biomechanical heart, in which the skeletal muscle is wrapped about a deformable training apparatus (2) adapted to contract, opposing a contraction resistance, and then resumes its initial shape and the skeletal muscle (1) is stimulated by means of periodic electric pulses (3) so as to effect its contraction and that of the deformable training apparatus (2) and their subsequent relaxation, characterized in that during a first stage the skeletal muscle (1)

is stimulated by means of electric pulses having a frequency increasing with time and during a second stage resistance of the deformable training apparatus (2) to contraction is progressively increased, the first and second stages if desired somewhat overlapping.

2. The process according to claim 1, characterized in that there is applied, to the muscle, during a relaxation phase following an electrical stimulation or contraction phase, a distension force acting in a direction opposite that of a contractive force.

3. Process according to claim 1, characterized in that there is used, between the muscle (1) and the deformable training apparatus (2), a layer of intermediate material (34) colonizable by conjunctive tissue.

4. The process according to claim 1 characterized in that the skeletal muscle (1) is first disposed within a tubular sleeve (32) preventing adherence of the muscle to surrounding tissues.

5. An implantable biomechanical heart operating from periodic contractions, under electrical stimulation impulses, of a driving skeletal muscle (1), characterized in that its drive muscle comprises a muscle (1) that has first been trained by the process according to claim 1, and characterized in that it further comprises an elastically deformable tubular cage (6, 30) having open ends, the tubular cage further having a central portion about which the muscle (1) is wrapped the cage being prolonged by two opposite end portions of a smaller diameter than the central portion.

6. The biomechanical heart according to claim 5, characterized in that the tubular cage (6) which constitutes a pumping cage of a ventricle with axial circulation of blood flow, comprises a flexible external envelope (7), several layers of curved springs (8), with outwardly directed convexity, extending over all a length of the envelope (7), from one end to another of the cage (6), and distributed about an axis of this cage (6), two transverse stretcher rings (9) disposed respectively in two open ends of the tubular cage (6) and in which are embedded ends of spring blades (8), an internal athrombogenic membrane extending within the cage (6) and covering said spring blades (8) to which it adheres so as to delimit between said spring blades (8) individual sealed chambers filled with a fluid (12).

7. The biomechanical heart according to claim 5, characterized in that it comprises a membrane (34) wrapped about an axle, with a continuous surface, open at its two ends, interposed between the muscle (1) and said deformable training apparatus (2) during a training period, the membrane (34) being of a material colonizable by conjunctive tissue to provide, after said training period, a flexible tubular cage (35) comprising on its outside the muscle (1) and on its inside the membrane (34) adhering to the muscle and colonized by cells of said conjunctive tissue.

8. The Biomechanical heart according to claim 5, characterized in that it constitutes a pericardiac device comprising a flexible and elastic tubular cage (30), open at its two ends, surrounded by the muscle (1), one of plural openings of the cage (30) having a diameter sufficiently great to permit introduction of a human heart within this cage, the muscle surrounding the tubular cage can be prolonged if it is too short by a resistant polymeric element (33) permitting it to surround completely this tubular cage.

9. The biomechanical heart according to claim 5, characterized in that it constitutes a ventricle with transverse circulation of blood flow comprising a flexible inexpansible pocket (19) adapted to be surrounded by the muscle (1) and extending within a hollow body (21) through an opening of this body, a sealed membrane (22) or a piston separating into two portions the hollow body (21) so as to delimit a pumping chamber (23) within the flexible pocket (19) containing a liquid, and an expulsion chamber (24), this expulsion chamber (34) being provided with two connections namely an inlet connection (25) provided with an inlet valve (26) and an outlet connection (27) provided with an outlet valve (28).

10. The Biomechanical heart according to claim 5, characterized in that it constitutes a pericardiac device comprising a flexible and elastic cage (37) forming a pumping chamber or a pressure pulse emitter, about which the muscle (1) will be wrapped, a pocket (39, 51) in which is disposed a human heart (15) and forming a receiver for pressure impulses and an expansible means (42, 49) connected to the cage (37) by a hydraulic transmission conduit (38), to effect contraction of the heart (15) during receipt of each pressure pulse.

11. The Biomechanical heart according to claim 10, characterized in that the pocket (39) in which the heart (15) is disposed, has a hollow wall and it comprises an inexpansible external envelope (41) and an internal expansible envelope (42) in contact with the heart.

12. The Biomechanical heart according to claim 10, characterized in that it comprises an external inexpansible pocket (51) within which are disposed the human heart (15) and an expansible envelope (49) in contact on the one hand with the external pocket (51) and on the other hand with the human heart (15).

13. The Biomechanical heart according to claim 10 characterized in that the conduit (38) extending between the flexible and elastic cage (37) forming the pumping chamber and the pocket (39, 51) in which is disposed the human heart (15), is connected by means of a branch conduit (43) to a chamber (44) located beneath the skin (45) of the patient enclosed by a preferable membrane (46) through which can be introduced a needle (47) for resupply of propulsive liquid and if desired a needle (48) for pressure measurement.

14. The biomechanical heart according to any one of claims 10 to 13, characterized in that a tube (52) is connected to the hydraulic transmission conduit (38) to remit the transcutaneous connection of a suction system and to permit the internal surface of the hydraulic pocket (39) to adhere permanently to the epicardium.

\* \* \* \* \*